(12) United States Patent
Walsdorff et al.

(10) Patent No.: US 7,193,121 B2
(45) Date of Patent: Mar. 20, 2007

(54) METHOD FOR PRODUCING 4-VINYLCYCLOHEXENE, ETHYL BENZOLE AND STYRENE

(75) Inventors: Christian Walsdorff, Ludwigshafen (DE); Götz-Peter Schindler, Mannheim (DE); Klaus Harth, Altleiningen (DE); Hartmut Hibst, Schriesheim (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 24 days.

(21) Appl. No.: 10/501,876

(22) PCT Filed: Feb. 17, 2003

(86) PCT No.: PCT/EP03/01577

§ 371 (c)(1),
(2), (4) Date: Jul. 20, 2004

(87) PCT Pub. No.: WO03/070671

PCT Pub. Date: Aug. 28, 2003

(65) Prior Publication Data

US 2004/0260132 A1    Dec. 23, 2004

(30) Foreign Application Priority Data

Feb. 19, 2002  (DE) .............................. 102 06 954
Jul. 12, 2002  (DE) .............................. 102 31 633

(51) Int. Cl.
*C07C 5/32*    (2006.01)
(52) U.S. Cl. .................... 585/324; 585/326; 585/319
(58) Field of Classification Search ............... 585/324, 585/326, 319
See application file for complete search history.

(56) References Cited

U.S. PATENT DOCUMENTS

| 2,376,985 | A |   | 5/1945  | Voorhees |
| 2,438,041 | A | * | 3/1948  | Dutcher ..................... 585/322 |
| 3,161,670 | A | * | 12/1964 | Adams et al. ............... 558/320 |
| 3,502,736 | A |   | 3/1970  | Sato et al. |
| 4,029,715 | A |   | 6/1977  | Rieve et al. |
| 5,196,621 | A |   | 3/1993  | Diesen et al. |
| 5,321,180 | A |   | 6/1994  | Davis |

FOREIGN PATENT DOCUMENTS

WO    94/01385    1/1994

* cited by examiner

*Primary Examiner*—Thuan Dinh Dang
(74) *Attorney, Agent, or Firm*—Novak Druce & Quigg LLP

(57) ABSTRACT

The invention relates to a process for preparing 4-vinylcyclohexene, which comprises the steps
  (A) providing an n-butane-containing feed gas stream,
  (B) feeding the n-butane-containing feed gas stream into at least one dehydrogenation zone and dehydrogenating n-butane to butadiene to give a product stream comprising butadiene, n-butane, possibly 1-butene and 2-butene and possibly water vapor and other secondary constituents,
  (C) feeding the product stream from dehydrogenation, if appropriate after separating off water vapor and secondary constituents, into a dimerization zone and catalytically dimerizing butadiene to give a product stream comprising 4-vinylcyclohexene, n-butane and possibly 1-butene, 2-butene and unreacted butadiene, and
  (D) separating off 4-vinylcyclohexene from the product stream from the dimerization and recirculating n-butane and possibly 1-butene, 2-butene and unreacted butadiene to the dehydrogenation zone.

6 Claims, 4 Drawing Sheets

METHOD FOR PRODUCING 4-VINYLCYCLOHEXENE, ETHYL BENZOLE AND STYRENE

The present invention relates to a process for preparing 4-vinylcyclohexene and for preparing ethylbenzene and styrene as downstream products of 4-vinylcyclohexene.

It is known that 4-vinylcyclohexene can be prepared by cyclodimerization of 1,3-butadiene in the liquid phase in the presence of supported catalysts comprising Cu(I) ions. The 4-vinylcyclohexene formed can be dehydrogenated to ethylbenzene in a downstream dehydrogenation step or oxydehydrogenated directly to styrene in the presence of oxygen.

U.S. Pat. No. 5,196,621 discloses a process for the dimerization of butadiene in the liquid phase over aluminosilicates impregnated with Cu(I) ions as dimerization catalysts, preferably over zeolites such as faujasite, mordenite, zeolite L, omega zeolite and beta zeolite which have been impregnated with Cu(I) ions. Furthermore, clay minerals such as montmorillonite containing Cu(I) ions and Cu(I)-containing nonzeolitic amorphous aluminum oxide/silicon dioxide mixtures, silicon dioxide or aluminum oxide are also mentioned as suitable catalysts.

Butadiene is prepared mainly by thermal cracking of saturated hydrocarbons, usually using naphtha as raw material. The cracking of naphtha gives a hydrocarbon mixture comprising methane, ethane, ethene, acetylene, propane, propene, propyne, allene, butenes, butadiene, butynes, methylallene, $C_5$-hydrocarbons and higher hydrocarbons. Acetylenically unsaturated hydrocarbons, in particular, in the cracking gas, e.g. acetylene, propyne, 1-butyne, 2-butyne, butenyne and diacetylene interfere in the dimerization. Even traces of these compounds can poison the copper-containing dimerization catalyst. Butynes and allenes likewise react with butadiene in a Diels-Alder reaction and lead to by-product formation. Particular problems are presented by the butynes which are very difficult to separate from butadiene by distillation or extraction. When using butadiene from crackers, it is therefore necessary to precede the butadiene dimerization by a hydrogenation step in which the butynes are selectively partially hydrogenated to the corresponding butenes. In other uses of butadiene, too, triply unsaturated $C_4$-hydrocarbons generally interfere.

A further disadvantage is that the cracking of naphtha or other hydrocarbon mixtures produces a complex hydrocarbon mixture. Thus, the production of butadiene in a cracking process inevitably leads to formation of relatively large amounts of ethene or propene as coproducts.

It is an object of the present invention to provide an economical process for preparing 4-vinylcyclohexene, ethylbenzene or styrene in which coproducts are formed to a lesser extent. A particular object of the invention is to provide a preparation of 4-vinylcyclohexene, ethylbenzene and styrene which has a new raw materials basis.

We have found that this object is achieved by a process for preparing 4-vinylcyclohexene, which comprises the steps (A) providing an n-butane-containing feed gas stream,
(B) feeding the n-butane-containing feed gas stream into at least one dehydrogenation zone and dehydrogenating n-butane to butadiene to give a product stream comprising butadiene, n-butane, possibly 1-butene and 2-butene and possibly water vapor and other secondary constituents,
(C) feeding the product stream from dehydrogenation, if appropriate after separating off water vapor and secondary constituents, into a dimerization zone and catalytically dimerizing butadiene to give a product stream comprising 4-vinylcyclohexene, n-butane and possibly 1-butene, 2-butene and unreacted butadiene, and
(D) separating off 4-vinylcyclohexene from the product stream from the dimerization and recirculating n-butane and possibly 1-butene, 2-butene and unreacted butadiene to the dehydrogenation zone.

No significant amounts of acetylenically unsaturated hydrocarbons or allenes are formed as by-products in the dehydrogenation of n-butane. Thus, a partial hydrogenation of the gas mixture used in the dimerization of butadiene can be omitted.

In a first process stage A, an n-butane-containing feed gas stream is provided. n-Butane-rich gas mixtures such as liquefied petroleum gas (LPG) are usually used as raw materials for this purpose. LPG consists essentially of $C_2$–$C_5$-hydrocarbons. The composition of LPG can fluctuate widely. The LPG used advantageously contains at least 10% by weight of butanes.

In one variant of the process of the present invention, the provision of the n-butane-containing dehydrogenation feed stream comprises the steps (A1) providing a liquefied petroleum gas (LPG) stream,
(A2) separating off propane and, if appropriate, methane, ethane and pentanes from the LPG stream to give a stream comprising butanes,
(A3) separating off isobutane from the stream comprising butanes to give the n-butane-containing feed gas stream and, if desired, isomerizing the isobutane which has been separated off to give an n-butane/isobutane mixture and recirculating the n-butane/isobutane mixture to the isobutane separation step.

Propane and, if appropriate, methane, ethane and pentanes are separated off in one or more customary rectification columns. For example, low boilers (methane, ethane, propane) can be separated off via the top in a first column and high boilers (pentanes) can be separated off at the bottom in a second column. This gives a stream comprising butanes (n-butane and isobutane) from which isobutane is separated off in a, for example, customary rectification column. The remaining n-butane-containing stream is used as feed gas stream for the subsequent dehydrogenation of butane.

The isobutane stream which has been separated off is preferably subjected to isomerization. For this purpose, the isobutane-containing stream is fed into an isomerization reactor. The isomerization of isobutane to n-butane can be carried out as described in GB-A 2 018 815. This gives an n-butane/isobutane mixture which is fed into the n-butane/isobutane separation column.

In a process stage (B), n-butane is dehydrogenated to butadiene.

In an embodiment of the process of the invention, the butadiene dehydrogenation is carried out as a nonoxidative catalytic dehydrogenation. In this, n-butane is partially dehydrogenated over a dehydrogenation-active catalyst in a dehydrogenation reactor to give butadiene. In addition, 1-butene and 2-butene are formed from n-butane. The dehydrogenation also results in the formation of hydrogen and small amounts of methane, ethane, ethene, propane and propene. Depending on the way in which the dehydrogenation is carried out, carbon oxides (CO, $CO_2$), water and nitrogen can also be present in the product gas mixture from the butane dehydrogenation. In addition, unreacted butane is present in the product gas mixture.

The nonoxidative catalytic dehydrogenation of butane can be carried out with or without the use of an oxygen-containing gas as cofeed.

The nonoxidative catalytic dehydrogenation of n-butane can in principle be carried out in all types of reactor known from the prior art and by all known modes of operation. A comparatively comprehensive description of dehydrogenation processes which are suitable for the purposes of the present invention is given in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

A suitable type of reactor is a fixed-bed tube or shell-and-tube reactor. In these, the catalyst (dehydrogenation catalyst and, when using oxygen as cofeed, possibly a specific oxidation catalyst) is present as a fixed bed in a reaction tube or in a bundle of reaction tubes. The reaction tubes are usually heated indirectly by a gas, e.g. a hydrocarbon such as methane, being burnt in the space surrounding the reaction tubes. It is advantageous to employ this indirect form of heating only over the first about 20–30% of the length of the fixed bed and to heat the remaining length of the bed to the required reaction temperature by means of the radiative heat produced as a result of the indirect heating. Customary internal diameters of the reaction tube(s) are from about 10 to 15 cm. A typical shell-and-tube dehydrogenation reactor comprises from about 300 to 1 000 reaction tubes. The temperature in the interior of the reaction tubes is usually in the range from 300 to 1 200° C., preferably in the range from 500 to 1000° C. The working pressure is usually in the range from 0.5 to 8 bar, frequently in the range from 1 to 2 bar, when using a small degree of steam dilution (as in the Linde process for propane dehydrogenation), but may also be in the range from 3 to 8 bar when using a high degree of steam dilution (as in the "steam active reforming process" (STAR process) of Phillips Petroleum Co. for the dehydrogenation of propane or butane, cf. U.S. Pat. Nos. 4,902,849, US 4,996,387 and US 5,389,342). Typical space velocities over the catalyst (GSHV) are from 500 to 2 000 h$^{-1}$, based on the hydrocarbon used. The catalyst geometry can be, for example, spherical or cylindrical (hollow or solid).

The nonoxidative catalytic dehydrogenation of n-butane can also be carried out in the presence of a heterogeneous catalyst in a fluidized bed, as described in Chem. Eng. Sci. 1992 b, 47 (9–11) 2313. It is advantageous to operate two fluidized beds in parallel, with one generally being in the regeneration mode. The working pressure is typically from 1 to 2 bar, and the dehydrogenation temperature is generally from 550 to 600° C. The heat required for the dehydrogenation is introduced into the reaction system by preheating the dehydrogenation catalyst to the reaction temperature. Mixing in an oxygen-containing cofeed can enable the preheater to be omitted and the required heat to be generated directly in the reactor system by combustion of hydrogen in the presence of oxygen. In addition, a hydrogen-containing cofeed can also be mixed in if appropriate.

The nonoxidative catalytic dehydrogenation of n-butane can be carried out with or without use of oxygen-containing gas as cofeed in a tray reactor. This contains one or more successive catalyst beds. The number of catalyst beds can be from 1 to 20, advantageously from 1 to 6, preferably from 1 to 4 and in particular from 1 to 3. The reaction gas preferably flows radially or axially through the catalyst beds. In general, such a tray reactor is operated using a fixed catalyst bed. In the simplest case, the fixed catalyst beds are installed axially or in the annular gaps of concentrically arranged cylindrical gratings in a shaft furnace reactor. One shaft furnace reactor corresponds to one tray. Carrying out the dehydrogenation in a single shaft furnace reactor corresponds to a preferred embodiment, with an oxygen-containing cofeed being able to be employed. In a further preferred embodiment, the dehydrogenation is carried out in a tray reactor having 3 catalyst beds. When the reactor is operated without oxygen-containing gas as cofeed, the reaction gas mixture is subjected to intermediate heating on its way from one catalyst bed to the next catalyst bed in the tray reactor, e.g. by passing it over heat exchanger surfaces heated by means of hot gases or by passing it through tubes heated by hot combustion gases.

In a preferred embodiment of the process of the present invention, the nonoxidative catalytic dehydrogenation of n-butane is carried out autothermally. For this purpose, additional oxygen is mixed into the reaction gas mixture of the n-butane dehydrogenation in at least one reaction zone and the hydrogen and/or hydrocarbons present in the reaction gas mixture is at least partially burnt so as to generate at least part of the required heat of dehydrogenation directly in the reaction gas mixture in the reaction zone or zones. A feature of autothermal operation compared to oxidative operation is, for example, the presence of hydrogen in the exit gas. In oxidative processes, no significant amounts of free hydrogen are formed.

In general, the amount of oxygen-containing gas added to the reaction gas mixture is chosen so that combustion of the hydrogen present in the reaction gas mixture and any hydrocarbons present in the reaction gas mixture and/or carbon present in the form of carbon deposits generates the heat necessary for the dehydrogenation of the n-butane. In general, the total amount of added oxygen is, based on the total amount of butane, from 0.001 to 0.5 mol/mol, preferably from 0.005 to 0.2 mol/mol, particularly preferably from 0.05 to 0.2 mol/mol. Oxygen can be used either as pure oxygen or in admixture with inert gases as an oxygen-containing gas, for example in the form of air. The inert gases and the resulting combustion gases generally have an additional diluting effect and thus aid the heterogeneously catalyzed dehydrogenation.

The hydrogen burned to generate heat is the hydrogen formed in the catalytic dehydrogenation of n-butane and also any additional hydrogen added as hydrogen-containing gas to the reaction gas mixture. Preference is given to adding such an amount of hydrogen that the molar ratio $H_2/O_2$ in the reaction gas mixture directly after the introduction of oxygen is from 1 to 10 mol/mol, preferably from 2 to 5 mol/mol. In the case of multistage reactors, this applies to each intermediate addition of oxygen-containing and, if applicable, hydrogen-containing gas.

The combustion of hydrogen occurs catalytically. The dehydrogenation catalyst used generally also catalyzes the combustion of hydrocarbons and of hydrogen with oxygen, so that in principle no specific oxidation catalyst other than this is necessary. In one embodiment, the dehydrogenation process is carried out in the presence of one or more oxidation catalysts which selectively catalyze the combustion of hydrogen to oxygen in the presence of hydrocarbons. As a result, the combustion of these hydrocarbons with oxygen to form CO, $CO_2$ and water occurs to only a minor extent. The dehydrogenation catalyst and the oxidation catalyst are preferably present in different reaction zones.

In the case of a multistage reaction, the oxidation catalyst can be present in only one reaction zone, in a plurality of reaction zones or in all reaction zones.

The catalyst which selectively catalyzes the oxidation of hydrogen is preferably located at places in which the oxygen partial pressure is higher than at other places in the reactor, in particular in the vicinity of the feed point for the oxygen-containing gas. The introduction of oxygen-containing gas and/or hydrogen-containing gas can be carried out at one or more points in the reactor.

In one embodiment of the process of the present invention, an intermediate addition of oxygen-containing gas and of hydrogen-containing gas is carried out upstream of each tray of a tray reactor. In a further embodiment of the process of the present invention, the introduction of oxygen-containing gas and of hydrogen-containing gas is carried out upstream of each tray apart from the first tray. In one embodiment, a bed of a specific oxidation catalyst is present downstream of each addition point, followed by a bed of the dehydrogenation catalyst. In a further embodiment, no specific oxidation catalyst is present. The dehydrogenation temperature is generally from 400 to 1 100° C., and the pressure in the last catalyst bed of the tray reactor is generally from 0.2 to 5 bar, preferably from 1 to 3 bar. The space velocity (GSHV) is generally from 500 to 2 000 $h^{-1}$, and in a high-load process even up to 100 000 $h^{-1}$, preferably from 4 000 to 16 000 $h^{-1}$.

A preferred catalyst which selectively catalyzes the combustion of hydrogen comprises oxides and/or phosphates selected from the group consisting of the oxides and phosphates of germanium, tin, lead, arsenic, antimony or bismuth. A further preferred catalyst which catalyzes the combustion of hydrogen comprises a noble metal of transition group VIII and/or I.

The dehydrogenation catalysts used generally comprise a support and an active composition. The support usually comprises a thermally stable oxide or mixed oxide. The dehydrogenation catalysts preferably comprise a metal oxide which is selected from the group consisting of zirconium dioxide, zinc oxide, aluminum oxide, silicon dioxide, titanium dioxide, magnesium oxide, lanthanum oxide, cerium oxide and mixtures thereof as support. The mixtures can be physical mixtures or chemical mixed phases such as magnesium- or zinc-aluminum mixed oxides. Preferred supports are zirconium dioxide and/or silicon dioxide, particularly preferably mixtures of zirconium dioxide and silicon dioxide.

The active composition of the dehydrogenation catalysts generally comprises one or more elements of transition group VIII, preferably platinum and/or palladium, particularly preferably platinum. The dehydrogenation catalysts can further comprise one or more elements of main groups I and/or II, preferably potassium and/or cesium. Furthermore, the dehydrogenation catalysts may also comprise one or more elements of transition group III including the lanthanides and actinides, preferably lanthanum and/or cerium. Finally, the dehydrogenation catalysts may comprise one or more elements of main groups III and/or IV, preferably one or more elements from the group consisting of boron, gallium, silicon, germanium, tin and lead, particularly preferably tin.

In a preferred embodiment, the dehydrogenation catalyst comprises at least one element of transition group VIII, at least one element of main groups I and/or II, at least one element of main groups III and/or IV and at least one element of transition group III including the lanthanides and actinides.

For the purposes of the present invention, it is possible to use, for example, all dehydrogenation catalysts disclosed in WO 99/46039, U.S. Pat. No. 4,788,371, EP-A 705 136, WO 99/29420, U.S. Pat. Nos. 5,220,091, US 5,430,220, US 5,877,369, EP 0 117 146, DE-A 199 37 106, DE-A 199 37 105 and DE-A 199 37 107.

Particularly preferred catalysts for the above-described variants of the autothermal dehydrogenation of butane are the catalysts described in examples 1, 2, 3 and 4 of DE-A 199 37 107.

The n-butane dehydrogenation is preferably carried out in the presence of steam. The added steam serves as heat carrier and aids the gasification of organic deposits on the catalysts, thus countering carbonization of the catalysts and increasing the operating life of the catalyst. The organic deposits are in this way converted into carbon monoxide and carbon dioxide and possibly water.

The dehydrogenation catalyst can be regenerated in a manner known per se. Thus, steam can be added to the reaction gas mixture or an oxygen-containing gas can be passed over the catalyst bed at elevated temperature from time to time so that the deposited carbon is burned off. The presence of steam acting as diluent also has a positive effect on the position of the chemical equilibrium, which is shifted to the side of the dehydrogenation products. If desired, a reduction using a hydrogen-containing gas may be carried out after the regeneration by means of steam.

The butane dehydrogenation gives a gas mixture comprising butadiene, 1-butene, 2-butene and unreacted n-butane together with secondary constituents. Usual secondary constituents are hydrogen, water vapor, nitrogen, CO and $CO_2$, methane, ethane, ethene, propane and propene. The composition of the gas mixture leaving the dehydrogenation stage can vary greatly as a function of the way in which the dehydrogenation is carried out. Thus, the preferred autothermal dehydrogenation with addition of oxygen and further hydrogen gives a product gas mixture having a comparatively high content of water vapor and carbon oxides. When no oxygen is added, the product gas mixture from the nonoxidative dehydrogenation has a comparatively high hydrogen content.

The product gas stream from the nonoxidative autothermal dehydrogenation of butane typically comprises from 0.1 to 15% by volume of butadiene, from 1 to 15% by volume of 1-butene, from 1 to 20% by volume of 2-butene, from 20 to 70% by volume of butane, from 5 to 70% by volume of water vapor, from 0 to 5% by volume of low-boiling hydrocarbons (methane, ethane, ethene, propane and propene), from 0 to 30% by volume of hydrogen, from 0 to 30% by volume of nitrogen and from 0 to 5% by volume of carbon oxide.

In a preferred embodiment, the nonoxidative catalytic dehydrogenation is followed by an oxidative dehydrogenation.

The dehydrogenation of n-butane to butadiene comprises, in this preferred embodiment, the steps (B1) feeding the n-butane-containing feed gas stream into a first dehydrogenation zone and catalytically, nonoxidatively dehydrogenating n-butane to 1-butene, 2-butene and possibly butadiene to give a product gas stream comprising n-butane, 1-butene, 2-butene, possibly butadiene and possibly secondary constituents, (B2) feeding the product gas stream comprising n-butane, 1-butene, 2-butene, possibly butadiene and possibly secondary constituents into a second dehydrogenation zone and oxidatively dehydrogenating 1-butene and 2-butene to butadiene to give a product gas stream comprising butadiene, n-butane, water vapor and possibly secondary constituents.

The catalytic nonoxidative dehydrogenation (B1) of n-butane to 1-butene, 2-butene and possibly butadiene is preferably carried out as described above as an autothermal dehydrogenation.

The oxydehydrogenation (B2) can in principle be carried out using all types of reactor and modes of operation known from the prior art, for example in a fluidized bed, in a tray furnace or in a fixed-bed tube or shell-and-tube reactor. Preference is given to using the latter in the process of the present invention. Carrying out the oxidative dehydrogenation requires a gas mixture which has a molar oxygen:n-butene ratio of at least 0.5. Preference is given to an oxygen:n-butene ratio of from 0.55 to 50. To set this value, the product gas mixture from the catalytic dehydrogenation is generally mixed with oxygen or an oxygen-containing gas, for example air. The oxygen-containing gas mixture obtained is then fed to the oxydehydrogenation.

Catalysts which are particularly useful for the oxidative dehydrogenation (oxydehydrogenation) of the n-butenes to 1,3-butadiene are generally based on an Mo—Bi—O-containing multimetal oxide system, which generally further comprises iron. In general, the catalyst system further comprises additional components from groups 1 to 15 of the Periodic Table, for example potassium, magnesium, zirconium, chromium, nickel, cobalt, cadmium, tin, lead, germanium, lanthanum, manganese, tungsten, phosphorus, cerium, aluminum or silicon.

Suitable catalysts and their preparation are described, for example, in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x+SiO_2$) and DE-A 24 40 329 ($Mo_{12}BiCo_{4.5}Ni_{2.5}Cr_3P_{0.5}K_{0.1}O_x$), which are hereby explicitly incorporated by reference.

The stoichiometry of the active composition of many of the multimetal oxide catalysts suitable for the oxyhydrogenation of the n-butenes to 1,3-butadiene have the formula (I)

$$Mo_{12}Bi_aFe_bCo_cNi_dCr_eX^1_fK_gO_x \qquad (I),$$

where the variables have the following meanings:
X¹=W, Xn, Mn, La, Ce, Ge, Ti, Zr, Hf, Nb, P, Si, Sb, Al, Cd and/or Mg;
a=0.5 to 5, preferably from 0.5 to 2;
b=0 to 5, preferably from 2 to 4;
c=0 to 10, preferably from 3 to 10;
d=0 to 10;
e=0 to 10, preferably from 0.1 to 4;
f=0 to 5, preferably from 0.1 to 2;
g=0 to 2, preferably from 0.01 to 1; and
x=a number which is determined by the valence and abundance of the elements other than oxygen in (I).

In the process of the present invention, preference is given to using an Mo—Bi—Fe—O-containing multimetal oxide system for the oxydehydrogenation, with particular preference being given to an Mo—Bi—Fe—Cr—O- or Mo—Bi—Fe—Zr—O-containing multimetal oxide system. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x+SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Co_{4.5}Ni_{2.5}Mn_{0.5}K_{0.1}O_x$ and $Mo_{12}BiFe_3Co_{4.5}Ni_{2.5}La_{0.5}K_{0.1}O_x$), U.S. Pat. No. 3,911,039 ($Mo_{12}BiFe_3Co_{4.5}Ni_{2.5}Sn_{0.5}K_{0.1}O_x$), DE-A-25 30 959 and DE-A-24 47 825 ($Mo_{12}BiFe_3Co_{4.5}Ni_{2.5}W_{0.5}K_{0.1}O_x$). The preparation and characterization of the abovementioned catalysts are comprehensively described in the documents cited, which are hereby explicitly incorporated by reference.

The catalyst for the oxydehydrogenation is generally used as shaped bodies having a mean size of above 2 mm. Due to the need to pay attention to the pressure drop during operation of the process, relatively small shaped bodies are generally unsuitable. Suitable shaped bodies which may be mentioned are, for example, pellets, cylinders, hollow cylinders, rings, spheres, rods, wagon wheels or extrudates. Special shapes such as "trilobes" and "tristars" (cf. EP-A-0 593 646) or shaped bodies having at least one recess on the outside (cf. U.S. Pat. No. 5,168,090) are likewise possible.

In general, the catalyst used can be employed as an all-active catalyst. In this case, the entire shaped catalyst body consists of the active composition, including any auxiliaries, e.g. graphite or pore formers, and further components. In particular, it has been found to be advantageous to use the Mo—Bi—Fe—O-containing catalyst which is preferably used for the oxydehydrogenation of the n-butenes to butadiene as an all-active catalyst. It is also possible to apply the active compositions of the catalysts to a support, for example an inorganic, oxidic shaped body. Such catalysts are generally referred to as coated catalysts.

The oxydehydrogenation of the n-butenes to butadiene is generally carried out at from 220 to 490° C., preferably 250 to 450° C. For practical reasons, it is usual to select a reactor inlet pressure which is sufficient to overcome the flow resistances present in the plant and the subsequent work-up. This reactor inlet pressure is generally from 0.005 to 1 MPa gauge pressure, preferably from 0.01 to 0.5 MPa gauge pressure. The gas pressure employed in the inlet region of the reactor naturally decreases over the overall bed of catalysts and inert components.

Coupling of the nonoxidative catalytic, preferably autothermal, dehydrogenation with the oxidative dehydrogenation of the n-butenes formed gives a very much higher yield of butadiene based on n-butane used. Furthermore, the nonoxidative dehydrogenation can be carried out under mild conditions. Comparable yields of butadiene would be able to be achieved by means of an exclusively nonoxidative dehydrogenation only at the expense of significantly reduced selectivities.

The product gas stream leaving the oxidative dehydrogenation comprises butadiene and unreacted n-butane together with water vapor. As secondary constituents, it generally further comprises carbon monoxide, carbon dioxide, nitrogen, oxygen, methane, ethane, ethene, propane and propene, possibly hydrogen and oxygen-containing hydrocarbons (organic oxygen compounds). It generally contains only small proportions of 1-butene and 2-butene.

The product gas stream leaving the oxidative dehydrogenation can comprise, for example, from 1 to 20% by volume of butadiene, from 0 to 1% by volume of 1-butene, from 0 to 1% by volume of 2-butene, from 0 to 50% by volume of n-butane, from 2 to 50% by volume of water vapor, from 0 to 5% by volume of low-boiling hydrocarbons (methane, ethane, ethene, propane and propene), from 0 to 20% by volume of hydrogen, from 0 to 90% by volume of nitrogen, from 0 to 5% by volume of carbon oxides and from 0 to 3% by weight of organic oxygen compounds.

After leaving the dehydrogenation stage(s), the hot gas mixture, which is generally at a temperature of from 500 to 650° C. when the dehydrogenation is carried out entirely autothermally and generally at from 220 to 490° C. when the autothermal dehydrogenation is followed by an oxidative dehydrogenation, is usually cooled by means of water. This results in water vapor and any high-boiling organic secondary constituents being condensed out. The low-boiling secondary constituents such as hydrogen, carbon monoxide, carbon dioxide, nitrogen, methane, ethane, ethene, propane and propene which are present in the dehydrogenation gas mixture in addition to butadiene, n-butane and possibly 1-butene and 2-butene are usually separated off from the $C_4$-hydrocarbons prior to the butadiene dimerization.

The low-boiling secondary constituents can be separated off by customary rectification methods.

The low-boiling secondary constituents can also be separated off by means of a high-boiling absorption medium in an absorption/desorption cycle. This separates essentially all low-boiling secondary constituents (nitrogen, argon, hydrogen, methane, ethane, ethene, propane, propene, carbon oxides, oxygen) from the product gas stream from the dehydrogenation of n-butane.

For this purpose, the $C_4$-hydrocarbons are absorbed in an inert absorption medium in an absorption stage so as to give an absorption medium laden with the $C_4$-hydrocarbons and an off-gas comprising the other secondary constituents. In a desorption stage, the $C_4$-hydrocarbons and traces of secondary constituents are liberated again from the absorption medium.

Inert absorption media used in the absorption stage are generally high-boiling nonpolar solvents in which the hydrocarbon mixture to be separated off has a significantly higher solubility than do the other constituents of the product gas mixture. The absorption can be carried out by simply passing the product gas mixture through the absorption medium. However, it can also be carried out in columns or in rotary absorbers. Absorption can be carried out in cocurrent, countercurrent or in the crossflow mode. Suitable absorption columns are, for example, tray columns having bubble cap trays, centrifugal trays and/or sieve trays, columns containing structured packing, e.g. sheet metal packing having a specific surface area of from 100 to 1 000 $m^2/m^3$, e.g. Mellapak® 250 Y, and columns packed with random packing elements. However, trickle and spray towers, graphite block absorbers, surface absorbers such as thick film absorbers and thin film absorbers and also rotary columns, plate scrubbers, cross-spray scrubbers and rotary scrubbers are also possible.

Suitable absorption media are comparatively nonpolar organic solvents, for example aliphatic $C_8$–$C_{18}$-alkenes, or aromatic hydrocarbons such as middle oil fractions from paraffin distillation or ethers having bulky groups, or mixtures of these solvents. A polar solvent such as dimethyl phthalate may also be added to these. Suitable absorption media also include esters of benzoic acid and phthalic acid with straight-chain $C_1$–$C_8$-alkanols, e.g. n-butyl benzoate, methyl benzoate, ethyl benzoate, dimethyl phthalate, diethyl phthalate, and also heat transfer fluids such as biphenyl and diphenyl ether, their chlorine derivatives and also triarylalkenes. One suitable absorption medium is a mixture of biphenyl and diphenyl ether, preferably in the azeotropic composition, for example the commercially available Diphyl®. This solvent mixture frequently contains from 0.1 to 25% by weight of dimethyl phthalate. Further suitable absorption media are octanes, nonanes, decanes, undecanes, dodecanes, tridecanes, tetradecanes, pentadecanes, hexadecanes, heptadecanes and octadecanes and fractions comprising predominantly these linear alkanes obtained from refinery streams.

For desorption, the laden absorption medium is heated and/or depressurized to a lower pressure. Alternatively, desorption can also be carried out by stripping or by a combination of depressurization, heating and stripping in one or more process steps. The absorption medium which has been regenerated in the desorption stage is returned to the absorption stage.

Organic oxygen compounds can be separated off from the remaining $C_4$-hydrocarbon-containing stream in a further separation step, which can likewise be configured as an absorption/desorption cycle or as a rectification. Organic oxygen compounds are, for example, furan and maleic anhydride.

The remaining stream, which consists essentially of butadiene, n-butane, 1-butene and 2-butene, is fed to the dimerization.

In a subsequent process stage (C), butadiene is dimerized catalytically to form 4-vinylcyclohexene.

The dimerization of butadiene can be carried out in the liquid phase over a copper-containing catalyst. Suitable dimerization catalysts are aluminosilicates impregnated with Cu(I) ions, for example zeolites such as faujasite, mordenite, zeolite L, omega zeolite or beta zeolite which have been impregnated with Cu(I) ions, as described in U.S. Pat. No. 5,196,621. Further suitable supports are clay minerals such as montmorillonite, nonzeolitic amorphous aluminum oxide/silicon dioxide mixtures, silicon dioxide or aluminum oxide.

The dimerization of butadiene can be carried out in all customary reaction apparatuses in a fixed-bed or suspension mode, for example in tube reactors, continuously operated stirred vessels or cascades of stirred vessels. The reaction temperature is typically from 70 to 170° C., preferably from 100 to 130° C., and the reaction pressure is from 7 to 70 bar, preferably from 20 to 35 bar.

4-Vinylcyclohexene is formed high selectively in the dimerization of butadiene. 1-Butene and 2-butene but also possible traces of propene generally do not react under the reaction conditions since they do not have a double bond which is activated for the Diels-Alder reaction.

The dimerization of butadiene can also be carried out, as described in EP-A 0 397 266, in the liquid phase in a suitable solvent using iron nitrosyl chloride, cobalt nitrosyl chloride or nickel nitrosyl chloride in the presence of carbon monoxide and tin, zinc, manganese and/or magnesium. Examples of suitable solvents are ethylene glycol dialkyl ethers or diethylene glycol dialkyl ethers, tetrahydrofuran and acetonitrile. The reaction temperature is generally from 20 to 175° C., and the reaction pressure is from 1 to 70 bar. The vinylcyclohexene formed can subsequently be separated from the solvent by distillation.

In a further process stage (D), 4-vinylcyclohexene is separated off from the product stream from the butadiene dimerization. The separation can be carried out in a customary rectification column. This generally gives a stream of crude 4-vinylcyclohexene which may contain small amounts of $C_8$-by-products and a $C_4$ stream comprising n-butane, 1-butene, 2-butene and unreacted butadiene. The $C_4$ stream can be recirculated to the n-butane dehydrogenation.

The 4-vinylcyclohexene obtained can, if appropriate after prior purification, subsequently be dehydrogenated to ethylbenzene or else oxydehydrogenated to styrene in the presence of oxygen.

The present invention therefore also provides a process for preparing ethyl benzene or styrene comprising the steps (A), (B), (C) and (D) as described above and the additional step (E) feeding 4-vinylcyclohexene into a further dehydrogenation zone and catalytically dehydrogenating it to ethylbenzene or oxydehydrogenating it in the presence of oxygen to give styrene.

The dehydrogenation of 4-vinylcyclohexene to ethylbenzene can, as described in WO 94/01385, be carried out in the gas phase over magnesium oxide, zinc oxide, calcium oxide, strontium oxide or barium oxide as catalyst. The dehydrogenation can be carried out in many suitable reactors, e.g. continuously operated fixed-bed or fluidized-bed reactors. The reaction temperature is generally from 400 to 625° C., preferably from 450 to 600° C., and the reaction pressure is generally from 1 to 25 bar, preferably from 1 to 10 bar.

The dehydrogenation of 4-vinylcyclohexene to ethylbenzene can also, as described in U.S. Pat. No. 3,903,185, be carried out at from 350 to 450° C. and a pressure of from 2.5 to 30 bar in the presence of hydrogen over a catalyst comprising one or more elements of transition groups VI to VIII or oxides thereof on an aluminum oxide support. Preferred catalysts are rhenium, palladium and/or platinum on aluminum oxide and cobalt oxide/molybdenum oxide on aluminum oxide.

The dehydrogenation of 4-vinylcyclohexene to ethylbenzene can also, as described in U.S. Pat. No. 4,029,715, be carried out at 400° C. and atmospheric pressure in the presence of an inert gas such as steam or nitrogen over cobalt molybdate/potassium oxide on aluminum oxide as catalyst.

Furthermore, the dehydrogenation of 4-vinylcyclohexene to ethylbenzene can be carried out in the gas phase at atmospheric pressure and temperatures of up to 300° C. over palladium on magnesium oxide as catalyst.

The dehydrogenation gives a crude ethylbenzene which comprises, as secondary constituents, unreacted 4-vinylcyclohexane and ethylcyclohexane as by-product.

The 4-vinylcyclohexene formed in the dimerization of butadiene can also be dehydrogenated in the presence of oxygen so as to convert it directly into styrene. Appropriate processes are described, for example, in U.S. Pat. No. 3,502,736 and DE-A 2 612 082.

In a modification of the above-described process, the dehydrogenation of 4-vinylcyclohexene to styrene is carried out together with the n-butane dehydrogenation. In this way, the separation of 4-vinylcyclohexene from the product stream from the dimerization can be dispensed with.

This comprises the steps
(A) providing an n-butane-containing feed gas stream,
(B') feeding the n-butane-containing feed gas stream and a 4-vinylcyclohexene-containing gas stream into a dehydrogenation zone and jointly dehydrogenating n-butane and 4-vinylcyclohexene in the presence of oxygen to give a product stream comprising styrene, butadiene, n-butane, 1-butene, 2-butene, possibly ethylbenzene and further secondary constituents,
(C') separating off styrene and, if applicable, ethylbenzene and further high-boiling secondary constituents from the product stream from the dehydrogenation,
(D') feeding the stream comprising butadiene, n-butane, 1-butene and 2-butene into a dimerization zone and catalytically dimerizing butadiene to give a product stream comprising 4-vinylcyclohexene, n-butane, 1-butene, 2-butene and possibly unreacted butadiene,
(E') isolating the 4-vinylcyclohexene-containing gas stream from the product stream from the dimerization and feeding it into the dehydrogenation zone.

Further high-boiling secondary constituents which can be formed in the dehydrogenation and are separated off together with styrene and, if applicable, ethylbenzene are xylenes, toluene and benzene.

Suitable catalysts for the joint dehydrogenation of n-butane and 4-vinylcyclohexane in the presence of oxygen are those of the above-described dehydrogenation catalysts which comprise a noble metal of transition group VIII, preferably platinum and/or palladium, on a support. In addition, the dehydrogenation catalysts may comprise one or more elements of main groups I and/or II, preferably potassium and/or cesium, one or more elements of transition group III including the lanthanides and actinides, preferably lanthanum and/or cerium, one or more elements of main groups III and/or IV, preferably boron, gallium, silicon, germanium, tin and/or lead, particularly preferably tin.

Preferred embodiments of the process of the present invention are illustrated below with reference to the drawings.

Figure 1:
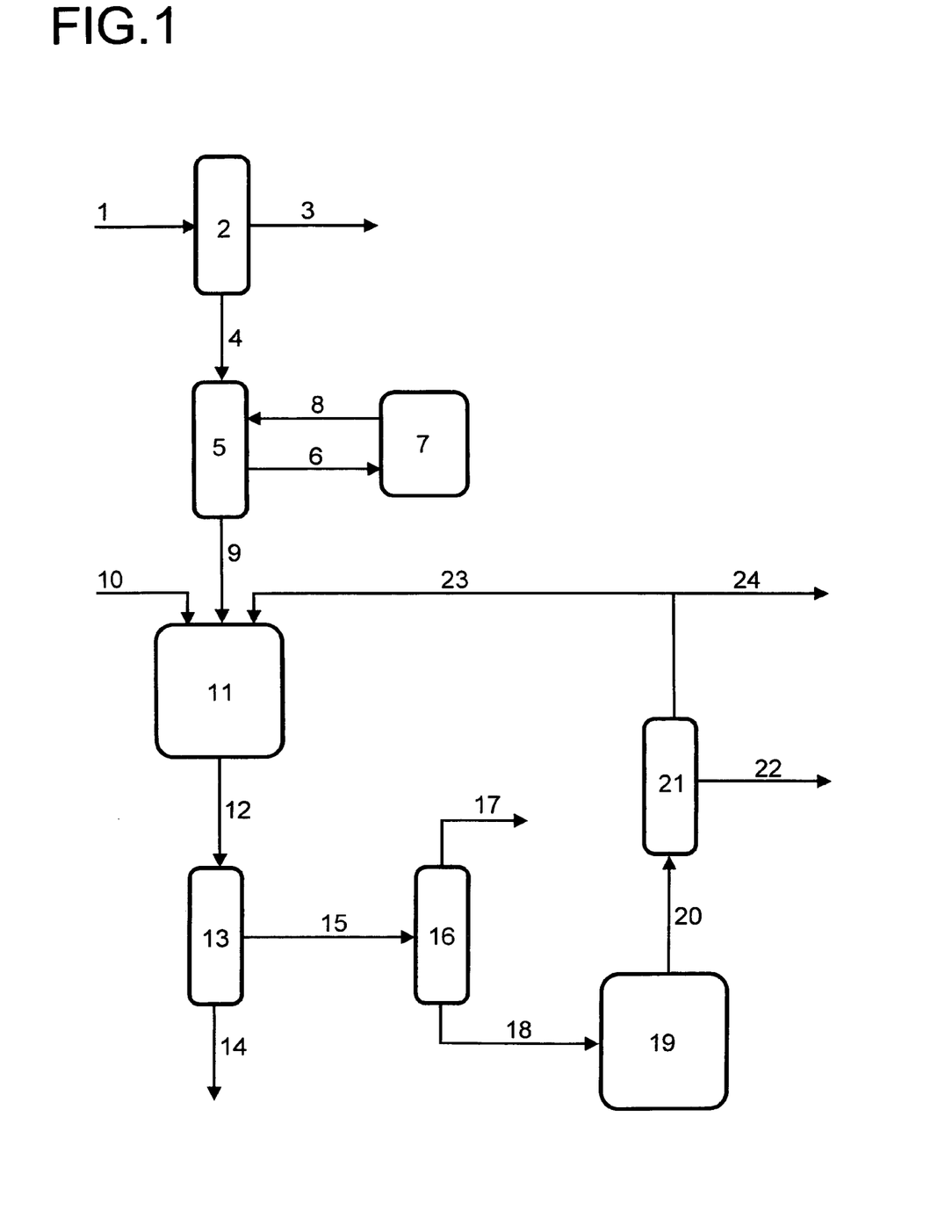

FIG. 1 shows the process flow diagram of a preferred embodiment of the process of the present invention. A feed stream 1 composed of liquefied petroleum gas (LPG), which consists essentially of propane, n-butane and isobutane, is fed into a rectification column 2 and separated into a stream 3 consisting essentially of propane and possibly methane and ethane and a stream 4 consisting essentially of n-butane and isobutane. In the rectification column 5, the butane mixture is separated into isobutane 6 and n-butane 9, with isobutane being isomerized in the isomerization reactor 7 to give an n-butane/isobutane mixture 8 which is fed back into the rectification column 5. n-Butane is introduced as feed gas stream 9 into the dehydrogenation reactor 11 which is preferably operated under autothermal conditions with addition of oxygen or air as cofeed 10. The product gas stream 12 leaving the dehydrogenation reactor, which comprises butadiene, 1-butene, 2-butene and unreacted n-butane together with by-products such as hydrogen, carbon oxides, nitrogen, water vapor, methane, ethane, ethene, propane and/or propene, is, after precooling in heat exchangers, cooled in the cooling and condensation unit 13, for example a bed through which water trickles or a falling film condenser, to such an extent that water and high-boiling organic by-products are condensed out and are discharged from the process as stream 14. The product of gas constituents which have not condensed out are passed as stream 15 to the separation stage 16 in which low boilers and incondensable secondary constituents 17 (one or preferably more components from the group consisting of hydrogen, carbon oxides, nitrogen, methane, ethane, ethene, propane and propene) are separated off. The separation stage 16 can be configured as a rectification column or as an absorption/desorption unit. The stream 18 which comprises the $C_4$ products of the dehydrogenation and unreacted n-butane is fed to the dimerization reactor 19 which can have one or more stages. The product stream 20 leaving the dimerization reactor is fractionated in the rectification column 21 to give a stream 22 comprising crude 4-vinylcyclohexene and a stream 23 comprising n-butane, 1-butene, 2-butene and possibly unreacted butadiene. The latter is recirculated to the dehydrogenation reactor 11. Optionally, a substream 24 can be separated off and be used in butene-based processes such as maleic anhydride production, the oxo process, butene dimerization, trimerization and metathesis.

Figure 2:
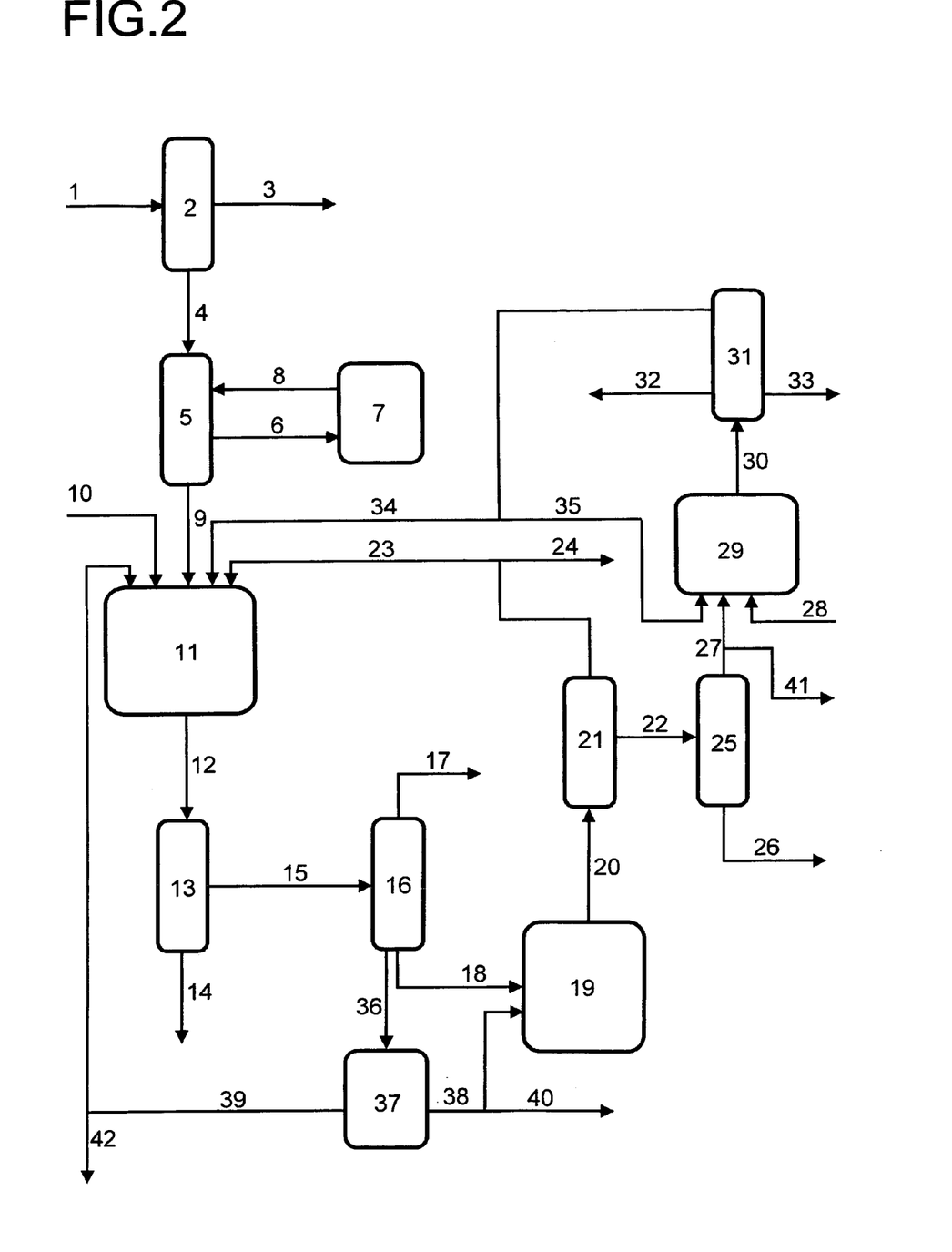

FIG. 2 shows the process flow diagram of a further preferred embodiment of the process of the present invention. This process differs from the process depicted in FIG. 1 essentially in that the dimerization of butadiene is followed by the dehydrogenation of the 4-vinylcyclohexene formed. The stream 22 comprising crude 4-vinylcyclohexene obtained from the rectification column 21 is optionally subjected to further purification in the rectification column 25, with a stream of high boilers 26 being separated off. The stream 27 composed of purified 4-vinylcyclohexene is fed to the dehydrogenation reactor 29 where the dehydrogenation to form ethylbenzene takes place in the presence of hydrogen 35 and steam 28. Optionally, a side stream 41 comprising 4-vinylcyclohexene can be taken off and passed to the catalytic oxydehydrogenation to form styrene or to another use. The product stream from the dehydrogenation of 4-vinylcyclohexene is cooled by means of water in the cooling and condensation unit 31 to give a stream 32 of aqueous phase and a stream 33 of crude ethylbenzene. The hydrogen formed in the dehydrogenation of 4-vinylcyclohexene, which may be contaminated with CO, $CO_2$, methane, ethane and nitrogen ("dehydrogenation hydrogen"), can be partly recirculated as substream 35 to the dehydrogenation reactor 29 and partly recirculated as substream 34 to the dehydrogenation reactor 11. Optionally, a substream 36 of the $C_4$ products separated off in the separation stage 16 can be fed to a further separation stage 37 and there separated into a stream 39 comprising 1-butene, 2-butene and n-butane and a stream 38 composed of butadiene. A substream 40 of butadiene can be taken from the stream 38 and passed to another use. The stream 39 can be recirculated at least partly to the dehydrogenation reactor, with a substream 42 being able to be passed to another use.

Figure 3:
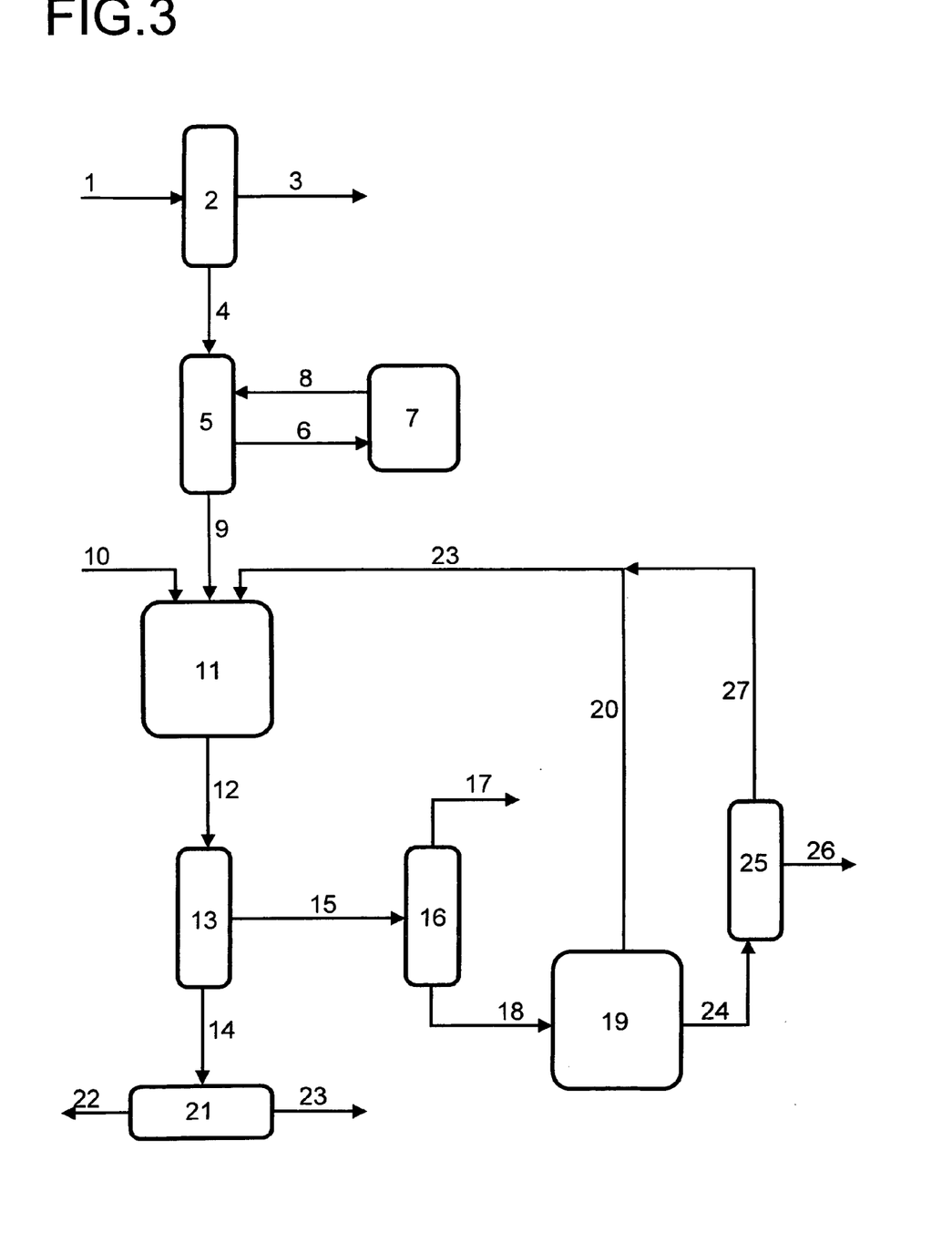

FIG. 3 shows the process flow diagram of a further embodiment of the process of the present invention. This process differs from the process depicted in FIG. 1 essentially in that the product stream 20 leaving the dimerization reactor, which comprises 4-vinylcyclohexene, n-butane, 1-butene, 2-butene and possibly unreacted butadiene, is fed into the dehydrogenation reactor 11 in which joint dehydrogenation of n-butane to butadiene and of 4-vinylcyclohexene to styrene takes place. Accordingly, water vapor and styrene vapor are condensed out from the product gas mixture 12 from the dehydrogenation in the cooling and condensation unit 13, passed as aqueous/organic mixture 14 to the phase separator 21 and there separated into an aqueous phase 22 and an organic phase 23 composed of crude styrene. Optionally, part of the product mixture obtained in the dimerization reactor 19 can be fed as stream 24 to a rectification column 25 where a stream 26 comprising $C_4$-hydrocarbons can be separated off and passed to another use. The remaining stream 27 comprising 4-vinylcyclohexene is fed to the dehydrogenation reactor 11.

Figure 4:
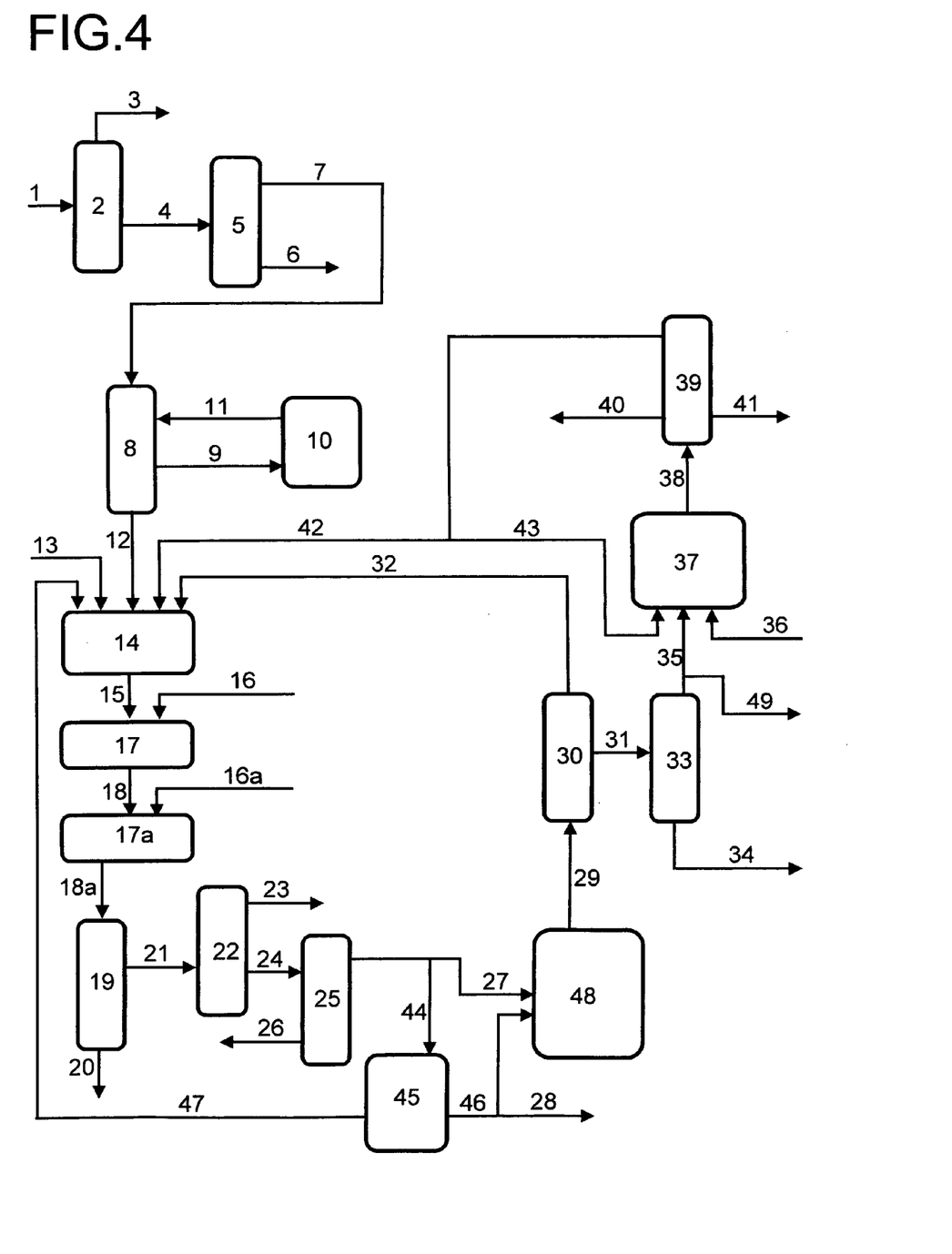

FIG. 4 shows the process flow diagram of a particularly preferred embodiment of the process of the present invention. A feed stream 1 composed of liquefied petroleum gas (LPG), which consists essentially of propane, n-butane and isobutane and may further comprise methane, ethane or pentanes, is fed to a rectification column 2 and separated into a stream 3 consisting essentially of propane and possibly methane and ethane and a stream 4 consisting essentially of n-butane and isobutane and possibly pentanes. In the rectification column 5, any pentanes 6 present are separated off. The butane mixture 7 is separated into isobutane 9 and n-butane 12 in the rectification column 8, with isobutane being isomerized in the isomerization reactor 10 to give an n-butane/isobutane mixture 11 which is fed back into the rectification column 8. n-Butane is fed as feed gas stream 12 into the first dehydrogenation stage 14 in which a nonoxidative catalytic dehydrogenation of butane to 1-butene, 2-butene and butadiene takes place. This is preferably carried out under autothermal conditions with oxygen or air being fed in as cofeed 13. The first dehydrogenation stage is preferably carried out with backmixing in the fluidized bed or with partial recirculation of the gas, for example as described in the German patent application P 102 11 275.4, which is not a prior publication. The product gas stream 15 leaving the first dehydrogenation stage, which comprises butadiene, 1-butene, 2-butene and unreacted n-butane together with water vapor and secondary constituents such as hydrogen, carbon oxides, nitrogen, methane, ethane, ethene, propane and/or propene, is passed to a second dehydrogenation stage 17 in which oxygen or air is fed in as cofeed and an oxidative dehydrogenation of 1-butane and 2-butene to butadiene takes place. The second dehydrogenation stage is preferably carried out in a shell-and-tube reactor. The second dehydrogenation stage can also itself be carried out in a plurality of stages, for example in two stages. When the oxidative dehydrogenation is carried out in two stages, the second dehydrogenation stage consists of a first oxidative dehydrogenation stage 17 and a second oxidative dehydrogenation stage 17a, with air or oxygen being fed in as cofeed 16 or 16a in each case. The product gas stream 18a leaving the second dehydrogenation stage (in the case of a single-stage oxidative dehydrogenation, this is the product gas stream 18) comprises butadiene and unreacted n-butane together with water vapor and secondary constituents such as hydrogen, carbon oxides, nitrogen, methane, ethane, ethene, propane and/or propene, possibly small residual amounts of 1-butene and 2-butene and possibly oxygen and oxygen-containing hydrocarbons (organic oxygen compounds). The product gas stream 18a is, if appropriate after precooling in heat exchangers, cooled in the cooling and condensation unit 19, which can, for example, be configured as a bed through which water trickles or as a falling-film condenser, to such an extent that water and high-boiling organic by-products such as high-boiling hydrocarbons and organic oxygen compounds are condensed out and are discharged from the process as stream 20. The product gas constituents which have not condensed out are passed as stream 21 to the separation stage 22 in which low boilers and incondensable secondary constituents 23 (if present in the product gas stream 18: hydrogen, carbon oxides, nitrogen, methane, ethane, ethene, propane, propene and oxygen) are separated off. The separation stage 22 can be configured as a rectification column or as an absorption/desorption unit. The stream 24 which comprises the $C_4$ products of the dehydrogenation, unreacted n-butane and possibly organic oxygen compounds such as furan and maleic anhydride is optionally fed to a further separation stage 25 which can be configured as a rectification column or an absorption/desorption unit. In the separation stage 25, organic oxygen compounds and any remaining traces of water are separated off and are discharged from the process as stream 26. The stream 27, which comprises butadiene and n-butane and may further comprise small proportions of 1-butene and 2-butene, is fed to the dimerization reactor 28 which can have one or more stages. The product stream 29 leaving the dimerization reactor, which may comprise as yet unreacted butadiene and small proportions of 1-butene and 2-butene in addition to n-butane and 4-vinylcyclohexene, is separated in the rectification column 30 into a stream 31 comprising crude 4-vinylcyclohexene and a stream 32 comprising n-butane and possibly unreacted butadiene, 1-butene and 2-butene. The stream 32 is recirculated to the (autothermal) dehydrogenation stage 14. The stream 31 comprising crude 4-vinylcyclohexene obtained in the rectification column 30 is optionally subjected to further purification in the rectification column 33 in which a stream 34 comprising high boilers is separated off. The stream 35 comprising purified 4-vinylcyclohexene is fed to the dehydrogenation reactor 37 where the dehydrogenation to ethylbenzene takes place in the presence of hydrogen 35 and with introduction of steam 36. Hydrogen 42 can be fed in if appropriate. If appropriate, a side stream 49 comprising 4-vinylcyclohexane can be taken off and passed to the catalytic oxydehydrogenation to form styrene or to another use. The product stream 38 from the 4-vinylhexene dehydrogenation is cooled by means of water in the cooling and condensation unit 39, giving a stream 41 composed of an aqueous phase and a stream 40 comprising crude ethylbenzene. The hydrogen formed in the dehydrogenation of 4-vinylcyclohexene, which may be contaminated by CO, $CO_2$, methane, ethane and nitrogen ("dehydrogenation hydrogen"), can be partly recirculated as substream 42 to the (autothermal) dehydrogenation stage 14 and partly recirculated as substream 43 to the dehydrogenation reactor 37. Optionally, a substream 44 of the $C_4$ products separated off in the separation stage 25 can be passed to a further separation stage 45, for example a butadiene scrub (as described in Weissermehl/Arpe, Industrielle Organische Chemie, 5th edition 1998, pp. 120/121) and separated there into a stream 47 comprising n-butane and possibly 1-butene and 2-butene and a stream 46 comprising butadiene. A substream 48 can be separated off from the butadiene stream 46 and passed to another use, while the remainder of the stream is fed to the dimerization reactor 28.

We claim:

1. A process for preparing 4-vinylcyclohexene, which comprises the steps
   (A) providing an n-butane-containing feed gas stream,
   (B) feeding the n-butane-containing feed gas stream into at least one dehydrogenation zone and dehydrogenating n-butane to butadiene to give a product stream comprising butadiene, n-butane, possibly 1-butene and 2-butene and possibly water vapor and other secondary constituents, said product stream not containing any significant amounts of acetylenically unsaturated hydrocarbons or allenes,
   (C) feeding the product stream from dehydrogenation, without prior partial hydrogenation of said product stream, and if appropriate after separating off water vapor and secondary constituents, into a dimerization zone and catalytically dimerizing butadiene to give a product stream comprising 4-vinylcyclohexene, n-butane and possibly 1-butene, 2-butene and unreacted butadiene, and
   (D) separating off 4-vinylcyclohexene from the product stream from the dimerization and recirculating n-butane and possibly 1-butene, 2-butene and unreacted butadiene to the dehydrogenation zone
   wherein the dehydrogenation of n-butane to butadiene comprises the steps
   (B1) feeding oxygen and the n-butane-containing feed gas stream into a first dehydrogenation zone and, in the presence of a dehydrogenation catalyst, nonoxidatively dehydrogenating n-butane to 1-butene, 2-butene and possibly butadiene to give a product gas stream comprising butadiene, n-butane, 1-butene, 2-butene and possibly secondary constituents,
   (B2) feeding the product gas stream comprising n-butane, 1-butene, 2-butene, possibly butadiene and possibly secondary constituents into a second dehydrogenation zone and oxidatively dehydrogenating 1-butene and 2-butene to butadiene to give a product gas stream comprising butadiene, n-butane, water vapor and possibly secondary constituents,
   wherein the catalytic, nonoxidative dehydrogenation of n-butane to 1-butene, 2-butene and butadiene is carried out as an autothermal dehydrogenation, and
   wherein the dehydrogenation catalyst in step (B1), comprises platinum and/or palladium.

2. A process as claimed in claim 1, wherein the provision of the n-butane-containing dehydrogenation feed stream comprises the steps
   (A1) providing a liquefied petroleum gas (LPG) stream,
   (A2) separating off propane and, if appropriate, methane, ethane and pentanes from the LPG stream to give a stream comprising butanes,
   (A3) separating off isobutane from the stream comprising butanes to give the n-butane-containing feed gas stream and, if desired, isomerizing the isobutane which has been separated off to give an n-butane/isobutane mixture and recirculating the n-butane/isobutane mixture to the isobutane separation step.

3. A process as claimed in claim 1, wherein water vapor and secondary constituents from the group consisting of hydrogen, carbon monoxide, carbon dioxide, nitrogen, methane, ethane, ethene, propane and propene are separated off from the product stream from the dehydrogenation prior to the dimerization.

4. A process for preparing ethylbenzene or styrene which comprises:
   firstly preparing 4-vinylcyclohexene in accordance with a process comprising
   (A) providing an n-butane-containing feed gas stream,
   (B) feeding the n-butane-containing feed gas stream into at least one dehydrogenation zone and dehydrogenating n-butane to butadiene to give a product stream comprising butadiene, n-butane, possibly 1-butene and 2-butene and possibly water vapor and other secondary constituents, said product stream not containing any significant amounts of acetylenically unsaturated hydrocarbons or allenes,
   (C) feeding the product stream from dehydrogenation, without prior partial hydrogenation of said product stream, and if appropriate after separating off water vapor and secondary constituents, into a dimerization zone and catalytically dimerizing butadiene to give a product stream comprising 4-vinylcyclohexene, n-butane and possibly 1-butene, 2-butene and unreacted butadiene, and
   (D) separating off 4-vinylcyclohexene from the product stream from the dimerization and recirculating n-butane and possibly 1-butene, 2-butene and unreacted butadiene to the dehydrogenation zone,
   and subsequently
   (E) feeding the 4-vinylcyclohexene into a further dehydrogenation zone and catalytically dehydrogenating it to ethylbenzene or oxidatively dehydrogenating it in the presence of oxygen to give styrene
   wherein the dehydrogenation of n-butane to butadiene comprises the steps
   (B1) feeding oxygen and the n-butane-containing feed gas stream into a first dehydrogenation zone and, in the presence of a dehydrogenation catalyst, nonoxidatively dehydrogenating n-butane to 1-butene, 2-butene and possibly butadiene to give a product gas stream comprising butadiene, n-butane, 1-butene, 2-butene and possibly secondary constituents,
   (B2) feeding the product gas stream comprising n-butane, 1-butene, 2-butene, possibly butadiene and possibly secondary constituents into a second dehydrogenation zone and oxidatively dehydrogenating 1-butene and 2-butene to butadiene to give a product gas stream comprising butadiene, n-butane, water vapor and possibly secondary constituents,
   wherein the catalytic, nonoxidative dehydrogenation of n-butane to 1-butene, 2-butene and butadiene is carried out as an autothermal dehydrogenation, and wherein the dehydrogenation catalyst in step (B1), comprises platinum and/or palladium.

5. A process for preparing styrene comprising the steps
(A) providing an n-butane-containing feed gas stream,
(B') feeding the n-butane-containing feed gas stream and a 4-vinylcyclohexene-containing gas stream into a dehydrogenation zone and jointly dehydrogenating n-butane and 4-vinylcyclohexene in the presence of oxygen to give a product stream comprising styrene, butadiene, n-butane, 1-butene, 2-butene, possibly ethylbenzene and further secondary constituents,
(C') separating off styrene and, if applicable, ethylbenzene and further high-boiling secondary constituents from the product stream from the dehydrogenation,
(D') feeding the stream comprising butadiene, n-butane, 1-butene and 2-butene into a dimerization zone and catalytically dimerizing butadiene to give a product stream comprising 4-vinylcyclohexene, n-butane, 1-butene, 2-butene and possibly unreacted butadiene,
(E') isolating the 4-vinylcyclohexene-containing gas stream from the product stream from the dimerization and feeding it into the dehydrogenation zone.

6. A process as claimed in claim 5, wherein the joint dehydrogenation of n-butane and 4-vinylcyclohexene is carried out in the presence of a dehydrogenation catalyst comprising a noble metal of transition group VIII together with, if desired, one or more elements of main groups I and/or II, one or more elements of main group III including the lanthanides and actinides and/or one or more elements of main groups III and/or IV on a support.

* * * * *